(12) United States Patent
Marsh et al.

(10) Patent No.: US 10,463,801 B2
(45) Date of Patent: Nov. 5, 2019

(54) METHOD FOR ASSEMBLING A DRIVE SPRING AND DRUG DELIVERY DEVICE WITH A SPRING

(71) Applicant: Sanofi, Paris (FR)

(72) Inventors: William Marsh, Buckingham (GB); Anthony Paul Morris, Coventry West Midlands (GB); Matthew Jones, Warwick (GB); Samuel Steel, Warwickshire (GB)

(73) Assignee: Sanofi, Paris (FR)

( * ) Notice: Subject to any disclaimer, the term of this patent is extended or adjusted under 35 U.S.C. 154(b) by 84 days.

(21) Appl. No.: 15/517,314

(22) PCT Filed: Oct. 9, 2015

(86) PCT No.: PCT/EP2015/073424
§ 371 (c)(1),
(2) Date: Apr. 6, 2017

(87) PCT Pub. No.: WO2016/055621
PCT Pub. Date: Apr. 14, 2016

(65) Prior Publication Data
US 2017/0296755 A1   Oct. 19, 2017

(30) Foreign Application Priority Data

Oct. 9, 2014 (EP) .................................... 14306587

(51) Int. Cl.
*A61M 5/315* (2006.01)
*A61M 5/20* (2006.01)
(Continued)

(52) U.S. Cl.
CPC ...... *A61M 5/31573* (2013.01); *A61M 5/2033* (2013.01); *A61M 5/31541* (2013.01);
(Continued)

(58) Field of Classification Search
CPC .... A61M 2005/202; A61M 2005/2026; A61M 2005/2407; A61M 2005/3126;
(Continued)

(56) References Cited

U.S. PATENT DOCUMENTS 9,821,121 B2 * 11/2017 Hirschel ........... A61M 5/31551
2012/0071836 A1 * 3/2012 Forstreuter ....... A61M 5/31515
604/208
(Continued)

FOREIGN PATENT DOCUMENTS

EP        2692376       2/2011
WO   WO 2008/145171   12/2008
(Continued)

OTHER PUBLICATIONS

International Preliminary Report on Patentability in International Application No. PCT/EP2015/073424, dated Apr. 11, 2017, 8 pages.
(Continued)

*Primary Examiner* — Quynh-Nhu H. Vu
(74) *Attorney, Agent, or Firm* — Fish & Richardson P.C.

(57) ABSTRACT

A method for assembling a drive spring, especially into a drug delivery device includes rotating a component part to which the drive spring is attached in a first direction, followed by a rotation of the component part in the opposite direction and followed by attachment of a rotational stop. Further, the disclosure includes a drug delivery device for selecting and dispensing a number of user variable doses of a medicament, which device comprises a pre-charged drive spring.

9 Claims, 2 Drawing Sheets (51) Int. Cl.
*A61M 5/31* (2006.01)
*A61M 5/24* (2006.01)

(52) U.S. Cl.
CPC .... *A61M 5/31551* (2013.01); *A61M 5/31553* (2013.01); *A61M 5/31561* (2013.01); *A61M 5/31583* (2013.01); *A61M 5/31585* (2013.01); *A61M 5/31593* (2013.01); *A61M 2005/202* (2013.01); *A61M 2005/2026* (2013.01); *A61M 2005/2407* (2013.01); *A61M 2005/3126* (2013.01); *A61M 2205/581* (2013.01); *A61M 2205/583* (2013.01); *A61M 2205/584* (2013.01); *A61M 2207/00* (2013.01)

(58) Field of Classification Search
CPC ...... A61M 2205/581; A61M 2205/583; A61M 2205/584; A61M 2207/00; A61M 5/2033; A61M 5/31541; A61M 5/31551; A61M 5/31553; A61M 5/31561; A61M 5/31573; A61M 5/31583; A61M 5/31585; A61M 5/31593
See application file for complete search history.

(56) References Cited

U.S. PATENT DOCUMENTS

| 2014/0039410 | A1 | 2/2014 | Harms et al. |
| 2014/0316347 | A1* | 10/2014 | Veasey ............ A61M 5/24 604/211 |
| 2016/0196716 | A1* | 7/2016 | Hughes ............ G07F 17/3265 463/20 |

FOREIGN PATENT DOCUMENTS

| WO | WO 2011/003979 | 1/2011 |
| WO | WO 2011/060785 | 5/2011 |
| WO | WO 2013/110538 | 8/2013 |
| WO | WO 2014/166908 | 10/2014 |

OTHER PUBLICATIONS

International Search Report and Written Opinion in International Application No. PCT/EP2015/073424, dated Dec. 11, 2015, 12 pages.

* cited by examiner

METHOD FOR ASSEMBLING A DRIVE SPRING AND DRUG DELIVERY DEVICE WITH A SPRING

CROSS-REFERENCE TO RELATED APPLICATIONS

This application is a U.S. national stage application under 35 USC § 371 of International Application No. PCT/EP2015/073424, filed on Oct. 9, 2015, which claims priority to European Patent Application No. 14306587.8, filed on Oct. 9, 2014, the entire contents of which are incorporated herein by reference.

TECHNICAL FIELD

The present disclosure is generally directed to a drug delivery device for selecting and dispensing a number of user variable doses of a medicament and to a method for assembling a drive spring for such a device.

BACKGROUND

Pen type drug delivery devices have application where regular injection by persons without formal medical training occurs. This may be increasingly common among patients having diabetes where self-treatment enables such patients to conduct effective management of their disease. In practice, such a drug delivery device allows a user to individually select and dispense a number of user variable doses of a medicament. The present disclosure is not directed to so called fixed dose devices which only allow dispensing of a predefined dose without the possibility to increase or decrease the set dose.

There are basically two types of drug delivery devices: resettable devices (i.e., reusable) and non-resettable (i.e., disposable). For example, disposable pen delivery devices are supplied as self-contained devices. Such self-contained devices do not have removable pre-filled cartridges. Rather, the pre-filled cartridges may not be removed and replaced from these devices without destroying the device itself. Consequently, such disposable devices need not have a resettable dose setting mechanism. The present disclosure is directed to reusable devices which allow resetting of the device and a replacement of a cartridge. Resetting of the device typically involves moving a piston rod or lead screw from an extended (distal) position, i.e. a position after dose dispensing, into a more retracted (proximal) position.

These types of pen delivery devices (so named because they often resemble an enlarged fountain pen) generally comprise three primary elements: a cartridge section that includes a cartridge often contained within a housing or holder; a needle assembly connected to one end of the cartridge section; and a dosing section connected to the other end of the cartridge section. A cartridge (often referred to as an ampoule) typically includes a reservoir that is filled with a medication (e.g., insulin), a movable rubber type bung or stopper located at one end of the cartridge reservoir, and a top having a pierceable rubber seal located at the other, often necked-down, end. A crimped annular metal band is typically used to hold the rubber seal in place. While the cartridge housing may be typically made of plastic, cartridge reservoirs have historically been made of glass.

The needle assembly is typically a replaceable double-ended needle assembly. Before an injection, a replaceable double-ended needle assembly is attached to one end of the cartridge assembly, a dose is set, and then the set dose is administered. Such removable needle assemblies may be threaded onto, or pushed (i.e., snapped) onto the pierceable seal end of the cartridge assembly.

The dosing section or dose setting mechanism is typically the portion of the pen device that is used to set (select) a dose. During an injection, a spindle or piston rod contained within the dose setting mechanism presses against the bung or stopper of the cartridge. This force causes the medication contained within the cartridge to be injected through an attached needle assembly. After an injection, as generally recommended by most drug delivery device and/or needle assembly manufacturers and suppliers, the needle assembly is removed and discarded.

A further differentiation of drug delivery device types refers to the drive mechanism: There are devices which are manually driven, e.g. by a user applying a force to an injection button, devices which are driven by a spring or the like and devices which combine these two concepts, i.e. spring assisted devices which still require a user to exert an injection force. The spring-type devices involve springs which are preloaded and springs which are loaded by the user during dose selecting. Some stored-energy devices use a combination of spring preload and additional energy provided by the user, for example during dose setting.

Unpublished patent application PCT/EP2014/056989 refers to a drug delivery device comprising a drive spring, which is a torsion spring attached with one end to the housing of the device and with its other end to a dose setting member which is rotatable with respect to the housing during dose setting and dose dispensing. A gauge element is interposed between the housing and the dose setting member. The gauge element is guided axially within the housing and is in threaded engagement with the dose setting member, such that the gauge element translates axially with respect to the housing and to the dose setting member upon a rotation of the dose setting member relative to the housing. The drive spring is strained (charged) during dose setting and releases stored energy during dose dispensing.

It is desirable to pre-charge the drive spring such that it provides sufficient torque even if only a small dose is to be dispensed, i.e. when the spring is only partly strained by the dose setting action. On the other hand, assembly of a pre-charge torsion spring is complicated, especially if the torsion spring is to be attached to a component part which is in threaded engagement with a further component part. Certain aspects of the present disclosure provide a method for assembling a spring driven drug delivery device which allows pre-charging of the drive spring during assembly and to provide such a drug delivery device.

SUMMARY

The method according to the disclosure preferably comprises the following steps: Attaching a torsion spring with one end to a first rotationally fixed component part, e.g. a housing, and with the other end to a rotatable component part, e.g. a number sleeve or dose setting member, wherein the rotatable component part is in threaded engagement with a second rotationally fixed component part, e.g. an axially movable gauge element, with a first rotational stop provided preventing rotation of the rotatable component part relative to the second rotationally fixed component part in a first spring releasing direction beyond the first rotational stop. Preferably, the spring is in a relaxed (uncharged) condition when being attached which facilitates mounting of the spring. Then, the rotatable component part is rotated away from the first rotational stop in a second spring charging direction until the rotatable component part disengages from the second rotationally fixed component part due to the threads disengaging. Rotation of the rotatable component part in the second spring charging direction is continued with the rotatable component part disengaged from the second rotationally fixed component part. This is followed by rotating the rotatable component part in the first spring releasing direction such that the rotatable component part re-engages the second rotationally fixed component part. Thereafter a second rotational stop is attached to the rotatable component part and/or the second rotationally fixed component part preventing rotation of the rotatable component part relative to the second rotationally fixed component part in the second spring charging direction beyond the second rotational stop. This method allows assembly and charging of the drive spring with minimum additional effort. In other words, it is a main idea of the present disclosure that a torsion spring which is fixed to a threaded component can be charged when fitted to a nut type component even when the number of charging turns required is greater than the travel of the nut, by allowing the nut to disengage the threaded component. Fitting an end stop after charging prevents disengagement of the nut, e.g. the gauge element, from the threaded component, e.g. the number sleeve or dose setting member, during later use of the device.

Preferably, the rotatable component part is positioned relative to the second rotationally fixed component part such that the first rotational stop is in effect, when rotation of the rotatable component part in the second spring charging direction begins. In other words, the rotatable component part and the second rotationally fixed component part are in an end position defined by the first rotational stop, which may be a minimum dose position (zero units dialed of a drug delivery device. This means that the spring is uncharged in this end position prior to the spring charging rotation of the rotatable component part, and is pre-charged (strained) when returning to this end position at the end of the assembly method.

The first rotationally fixed component part, e.g. the housing, may be rotationally coupled to the second rotationally fixed component part, e.g. the gauge element, to prevent relative rotation. However, relative axial movement may be allowed. Further, the second rotationally fixed component part, e.g. the gauge element, may be allowed to perform a small rotational movement when reaching or being at an end position, while being generally guided rotationally constrained to the housing.

It is preferred if at least during the rotation in the spring charging direction the rotatable component part is engaged by a rotatable tool while the first rotationally fixed component part is rotationally constrained by a further tool. Relative rotation of the two tools then charges the spring. Thus, spring charging may be an automated process step during assembly of a drug delivery device.

Rotation of the rotatable component part in the first spring releasing direction may be effected by the torsion spring. In other words, the rotatable component part may simply be released to allow the torsion spring to wind back the rotatable component part. Alternatively, the rotatable component part may be rotated by the rotatable tool. Preferably, the rotatable component part is rotated in the first spring releasing direction until the first rotational stop prevents rotation of the rotatable component part relative to the second rotationally fixed component part in a first spring releasing direction.

The second rotational stop is preferably permanently attached to the rotatable component part, e.g. by a snap-attachment or by gluing, welding or the like. This prevents unintended detachment of the mechanism.

The torsion spring may be axially compressed between the first rotationally fixed component part and the rotatable component part either during attachment or at a later stage, e.g. during charging. The axial load of the spring may be used to hold further component parts in place and/or such that the drive spring additionally acts as a clutch spring and/or a trigger spring.

The method according to the disclosure may be part of a method for assembling a drug delivery device, which may further comprise the steps of assembling a cartridge holder, a piston rod, a drive sleeve, a nut, a button, a dose selector, a clutch plate and/or a clutch spring. The first rotationally fixed component part may be the housing of the drug delivery device, the rotatable component part is preferably a number sleeve or dose setting member and the second rotationally fixed component part may be an axially movable gauge element.

A drug delivery device for selecting and dispensing a number of user variable doses of a medicament may comprise a drive spring, which is preferably a torsion spring, a rotationally fixed housing, a rotatable number sleeve, which is preferably rotatable during dose setting, dose correction and dose dispensing and axially constrained to the housing, and a rotationally fixed gauge element, which is in threaded engagement with the rotatable number sleeve and guided axially displaceable within the housing. Preferably, the drive spring is a pre-charged torsion spring attached with one end to the housing and with the other end to the number sleeve. According to an aspect of the present disclosure rotational movement of the number sleeve relative to the gauge element is limited in a first spring releasing direction by a first rotational stop and in a second spring charging direction by a second rotational stop which is a separate component part permanently attached to the number sleeve and/or the gauge element. This allows charging of the spring in an assembly state with the second rotational stop not yet attached to the number sleeve and/or the gauge element.

A piston rod may be coupled to the housing, such that the piston rod is movable relative to the housing driven by the drive spring. Preferably, the piston rod is in threaded engagement with the housing, wherein the spring driven movement of the piston rod is a combined rotation and axial displacement. As an alternative, the piston rod may be guided in the housing such that the piston rod is rotationally constrained to the housing but allowed to be displaced axially. The piston may be directly driven by the spring or, which is preferred, indirectly with at least one component part interposed between the piston rod and the spring. For example, a drive sleeve may be interposed between the piston rod and the number sleeve, which drive sleeve is movable relative to the housing driven by the drive spring. Preferably, the movement of the drive sleeve caused by the drive spring is a rotation.

In a preferred embodiment, the drive sleeve is axially movable relative to the housing between a dose setting position in which the drive sleeve is rotationally constrained to the housing and a dose dispensing position in which the drive sleeve is rotationally decoupled from the housing. In other words, axial movement of the drive sleeve may be used to switch a drug delivery device between a dose setting (and dose correcting) mode and a dose dispensing mode.

The drug delivery device may further comprise a clutch interposed between the number sleeve and the drive sleeve. Preferably, the clutch rotationally couples the number sleeve and the drive sleeve during dose dispensing and rotationally decouples the number sleeve and the drive sleeve during dose setting (and dose correcting).

The drug delivery device may further comprise a cartridge containing a medicament. The term "medicament", as used herein, means a pharmaceutical formulation containing at least one pharmaceutically active compound, wherein in one embodiment the pharmaceutically active compound has a molecular weight up to 1500 Da and/or is a peptide, a protein, a polysaccharide, a vaccine, a DNA, a RNA, an enzyme, an antibody or a fragment thereof, a hormone or an oligonucleotide, or a mixture of the above-mentioned pharmaceutically active compound, wherein in a further embodiment the pharmaceutically active compound is useful for the treatment and/or prophylaxis of diabetes mellitus or complications associated with diabetes mellitus such as diabetic retinopathy, thromboembolism disorders such as deep vein or pulmonary thromboembolism, acute coronary syndrome (ACS), angina, myocardial infarction, cancer, macular degeneration, inflammation, hay fever, atherosclerosis and/or rheumatoid arthritis, wherein in a further embodiment the pharmaceutically active compound comprises at least one peptide for the treatment and/or prophylaxis of diabetes mellitus or complications associated with diabetes mellitus such as diabetic retinopathy, wherein in a further embodiment the pharmaceutically active compound comprises at least one human insulin or a human insulin analogue or derivative, glucagon-like peptide (GLP-1) or an analogue or derivative thereof, or exendin-3 or exendin-4 or an analogue or derivative of exendin-3 or exendin-4.

Insulin analogues are for example Gly(A21), Arg(B31), Arg(B32) human insulin; Lys(B3), Glu(B29) human insulin; Lys(B28), Pro(B29) human insulin; Asp(B28) human insulin; human insulin, wherein proline in position B28 is replaced by Asp, Lys, Leu, Val or Ala and wherein in position B29 Lys may be replaced by Pro; Ala(B26) human insulin; Des(B28-B30) human insulin; Des(B27) human insulin and Des(B30) human insulin.

Insulin derivates are for example B29-N-myristoyl-des(B30) human insulin; B29-N-palmitoyl-des(B30) human insulin; B29-N-myristoyl human insulin; B29-N-palmitoyl human insulin; B28-N-myristoyl LysB28ProB29 human insulin; B28-N-palmitoyl-LysB28ProB29 human insulin; B30-N-myristoyl-ThrB29LysB30 human insulin; B30-N-palmitoyl-ThrB29LysB30 human insulin; B29-N—(N-palmitoyl-Y-glutamyl)-des(B30) human insulin; B29-N—(N-lithocholyl-Y-glutamyl)-des(B30) human insulin; B29-N-(ω-carboxyheptadecanoyl)-des(B30) human insulin and B29-N-(ω-carboxyheptadecanoyl) human insulin.

Exendin-4 for example means Exendin-4(1-39), a peptide of the sequence H-His-Gly-Glu-Gly-Thr-Phe-Thr-Ser-Asp-Leu-Ser-Lys-Gln-Met-Glu-Glu-Glu-Ala-Val-Arg-Leu-Phedle-Glu-Trp-Leu-Lys-Asn-Gly-Gly-Pro-Ser-Ser-Gly-Ala-Pro-Pro-Pro-Ser-NH2.

Exendin-4 derivatives are for example selected from the following list of compounds:

H-(Lys)4-des Pro36, des Pro37 Exendin-4(1-39)-NH2,
H-(Lys)5-des Pro36, des Pro37 Exendin-4(1-39)-NH2,
des Pro36 Exendin-4(1-39),
des Pro36 [Asp28] Exendin-4(1-39),
des Pro36 [IsoAsp28] Exendin-4(1-39),
des Pro36 [Met(O)14, Asp28] Exendin-4(1-39),
des Pro36 [Met(O)14, IsoAsp28] Exendin-4(1-39),
des Pro36 [Trp(O2)25, Asp28] Exendin-4(1-39),
des Pro36 [Trp(O2)25, IsoAsp28] Exendin-4(1-39),
des Pro36 [Met(O)14 Trp(O2)25, Asp28] Exendin-4(1-39),
des Pro36 [Met(O)14 Trp(O2)25, IsoAsp28] Exendin-4(1-39); or
des Pro36 [Asp28] Exendin-4(1-39),
des Pro36 [IsoAsp28] Exendin-4(1-39),
des Pro36 [Met(O)14, Asp28] Exendin-4(1-39),
des Pro36 [Met(O)14, IsoAsp28] Exendin-4(1-39),
des Pro36 [Trp(O2)25, Asp28] Exendin-4(1-39),
des Pro36 [Trp(O2)25, IsoAsp28] Exendin-4(1-39),
des Pro36 [Met(O)14 Trp(O2)25, Asp28] Exendin-4(1-39),
des Pro36 [Met(O)14 Trp(O2)25, IsoAsp28] Exendin-4(1-39), wherein the group -Lys6-NH2 may be bound to the C-terminus of the Exendin-4 derivative;

or an Exendin-4 derivative of the sequence
des Pro36 Exendin-4(1-39)-Lys6-NH2 (AVE0010),
H-(Lys)6-des Pro36 [Asp28] Exendin-4(1-39)-Lys6-NH2,
des Asp28 Pro36, Pro37, Pro38Exendin-4(1-39)-NH2,
H-(Lys)6-des Pro36, Pro38 [Asp28] Exendin-4(1-39)-NH2,
H-Asn-(Glu)5des Pro36, Pro37, Pro38 [Asp28] Exendin-4(1-39)-NH2,
des Pro36, Pro37, Pro38 [Asp28] Exendin-4(1-39)-(Lys)6-NH2,
H-(Lys)6-des Pro36, Pro37, Pro38 [Asp28] Exendin-4(1-39)-(Lys)6-NH2,
H-Asn-(Glu)5-des Pro36, Pro37, Pro38 [Asp28] Exendin-4(1-39)-(Lys)6-NH2,
H-(Lys)6-des Pro36 [Trp(O2)25, Asp28] Exendin-4(1-39)-Lys6-NH2,
H-des Asp28 Pro36, Pro37, Pro38 [Trp(O2)25] Exendin-4(1-39)-NH2,
H-(Lys)6-des Pro36, Pro37, Pro38 [Trp(O2)25, Asp28] Exendin-4(1-39)-NH2,
H-Asn-(Glu)5-des Pro36, Pro37, Pro38 [Trp(O2)25, Asp28] Exendin-4(1-39)-NH2,
des Pro36, Pro37, Pro38 [Trp(O2)25, Asp28] Exendin-4(1-39)-(Lys)6-NH2,
H-(Lys)6-des Pro36, Pro37, Pro38 [Trp(O2)25, Asp28] Exendin-4(1-39)-(Lys)6-NH2,
H-Asn-(Glu)5-des Pro36, Pro37, Pro38 [Trp(O2)25, Asp28] Exendin-4(1-39)-(Lys)6-NH2,
H-(Lys)6-des Pro36 [Met(O)14, Asp28] Exendin-4(1-39)-Lys6-NH2,
des Met(O)14 Asp28 Pro36, Pro37, Pro38 Exendin-4(1-39)-NH2,
H-(Lys)6-desPro36, Pro37, Pro38 [Met(O)14, Asp28] Exendin-4(1-39)-NH2,
H-Asn-(Glu)5-des Pro36, Pro37, Pro38 [Met(O)14, Asp28] Exendin-4(1-39)-NH2,
des Pro36, Pro37, Pro38 [Met(O)14, Asp28] Exendin-4(1-39)-(Lys)6-NH2,
H-(Lys)6-des Pro36, Pro37, Pro38 [Met(O)14, Asp28] Exendin-4(1-39)-(Lys)6-NH2,
H-Asn-(Glu)5 des Pro36, Pro37, Pro38 [Met(O)14, Asp28] Exendin-4(1-39)-(Lys)6-NH2,
H-Lys6-des Pro36 [Met(O)14, Trp(O2)25, Asp28] Exendin-4(1-39)-Lys6-NH2,
H-des Asp28 Pro36, Pro37, Pro38 [Met(O)14, Trp(O2)25] Exendin-4(1-39)-NH2,
H-(Lys)6-des Pro36, Pro37, Pro38 [Met(O)14, Asp28] Exendin-4(1-39)-NH2,
H-Asn-(Glu)5-des Pro36, Pro37, Pro38 [Met(O)14, Trp(O2)25, Asp28] Exendin-4(1-39)-NH2,
des Pro36, Pro37, Pro38 [Met(O)14, Trp(O2)25, Asp28] Exendin-4(1-39)-(Lys)6-NH2,
H-(Lys)6-des Pro36, Pro37, Pro38 [Met(O)14, Trp(O2)25, Asp28] Exendin-4(S1-39)-(Lys)6-NH2, H-Asn-(Glu)5-des Pro36, Pro37, Pro38 [Met(O)14, Trp(O2) 25, Asp28] Exendin-4(1-39)-(Lys)6-NH2;

or a pharmaceutically acceptable salt or solvate of any one of the afore-mentioned Exendin-4 derivative.

Hormones are for example hypophysis hormones or hypothalamus hormones or regulatory active peptides and their antagonists as listed in Rote Liste, ed. 2008, Chapter 50, such as Gonadotropine (Follitropin, Lutropin, Choriongonadotropin, Menotropin), Somatropine (Somatropin), Desmopressin, Terlipressin, Gonadorelin, Triptorelin, Leuprorelin, Buserelin, Nafarelin, Goserelin.

A polysaccharide is for example a glucosaminoglycane, a hyaluronic acid, a heparin, a low molecular weight heparin or an ultra low molecular weight heparin or a derivative thereof, or a sulphated, e.g. a poly-sulphated form of the above-mentioned polysaccharides, and/or a pharmaceutically acceptable salt thereof. An example of a pharmaceutically acceptable salt of a poly-sulphated low molecular weight heparin is enoxaparin sodium.

Antibodies are globular plasma proteins (~150 kDa) that are also known as immunoglobulins which share a basic structure. As they have sugar chains added to amino acid residues, they are glycoproteins. The basic functional unit of each antibody is an immunoglobulin (Ig) monomer (containing only one Ig unit); secreted antibodies can also be dimeric with two Ig units as with IgA, tetrameric with four Ig units like teleost fish IgM, or pentameric with five Ig units, like mammalian IgM.

The Ig monomer is a "Y"-shaped molecule that consists of four polypeptide chains; two identical heavy chains and two identical light chains connected by disulfide bonds between cysteine residues. Each heavy chain is about 440 amino acids long; each light chain is about 220 amino acids long. Heavy and light chains each contain intrachain disulfide bonds which stabilize their folding. Each chain is composed of structural domains called Ig domains. These domains contain about 70-110 amino acids and are classified into different categories (for example, variable or V, and constant or C) according to their size and function. They have a characteristic immunoglobulin fold in which two β sheets create a "sandwich" shape, held together by interactions between conserved cysteines and other charged amino acids.

There are five types of mammalian Ig heavy chain denoted by α, δ, ε, γ, and μ. The type of heavy chain present defines the isotype of antibody; these chains are found in IgA, IgD, IgE, IgG, and IgM antibodies, respectively.

Distinct heavy chains differ in size and composition; α and γ contain approximately 450 amino acids and δ approximately 500 amino acids, while p and E have approximately 550 amino acids. Each heavy chain has two regions, the constant region (CH) and the variable region (VH). In one species, the constant region is essentially identical in all antibodies of the same isotype, but differs in antibodies of different isotypes. Heavy chains γ, α and δ have a constant region composed of three tandem Ig domains, and a hinge region for added flexibility; heavy chains μ and ε have a constant region composed of four immunoglobulin domains. The variable region of the heavy chain differs in antibodies produced by different B cells, but is the same for all antibodies produced by a single B cell or B cell clone. The variable region of each heavy chain is approximately 110 amino acids long and is composed of a single Ig domain.

In mammals, there are two types of immunoglobulin light chain denoted by λ and κ. A light chain has two successive domains: one constant domain (CL) and one variable domain (VL). The approximate length of a light chain is 211 to 217 amino acids. Each antibody contains two light chains that are always identical; only one type of light chain, κ or λ, is present per antibody in mammals.

Although the general structure of all antibodies is very similar, the unique property of a given antibody is determined by the variable (V) regions, as detailed above. More specifically, variable loops, three each the light (VL) and three on the heavy (VH) chain, are responsible for binding to the antigen, i.e. for its antigen specificity. These loops are referred to as the Complementarity Determining Regions (CDRs). Because CDRs from both VH and VL domains contribute to the antigen-binding site, it is the combination of the heavy and the light chains, and not either alone, that determines the final antigen specificity.

An "antibody fragment" contains at least one antigen binding fragment as defined above, and exhibits essentially the same function and specificity as the complete antibody of which the fragment is derived from. Limited proteolytic digestion with papain cleaves the Ig prototype into three fragments. Two identical amino terminal fragments, each containing one entire L chain and about half an H chain, are the antigen binding fragments (Fab). The third fragment, similar in size but containing the carboxyl terminal half of both heavy chains with their interchain disulfide bond, is the crystalizable fragment (Fc). The Fc contains carbohydrates, complement-binding, and FcR-binding sites. Limited pepsin digestion yields a single F(ab')2 fragment containing both Fab pieces and the hinge region, including the H—H interchain disulfide bond. F(ab')2 is divalent for antigen binding. The disulfide bond of F(ab')2 may be cleaved in order to obtain Fab'. Moreover, the variable regions of the heavy and light chains can be fused together to form a single chain variable fragment (scFv).

Pharmaceutically acceptable salts are for example acid addition salts and basic salts. Acid addition salts are e.g. HCl or HBr salts. Basic salts are e.g. salts having a cation selected from alkali or alkaline, e.g. Na+, or K+, or Ca2+, or an ammonium ion N+(R1)(R2)(R3)(R4), wherein R1 to R4 independently of each other mean: hydrogen, an optionally substituted C1-C6-alkyl group, an optionally substituted C2-C6-alkenyl group, an optionally substituted C6-C10-aryl group, or an optionally substituted C6-C10-heteroaryl group. Further examples of pharmaceutically acceptable salts are described in "Remington's Pharmaceutical Sciences" 17. ed. Alfonso R. Gennaro (Ed.), Mark Publishing Company, Easton, Pa., U.S.A., 1985 and in Encyclopedia of Pharmaceutical Technology.

Pharmaceutically acceptable solvates are for example hydrates.

BRIEF DESCRIPTION OF THE DRAWINGS

Non-limiting, exemplary embodiments of the disclosure will now be described with reference to the accompanying drawings, in which.

DETAILED DESCRIPTION

Figure 1:
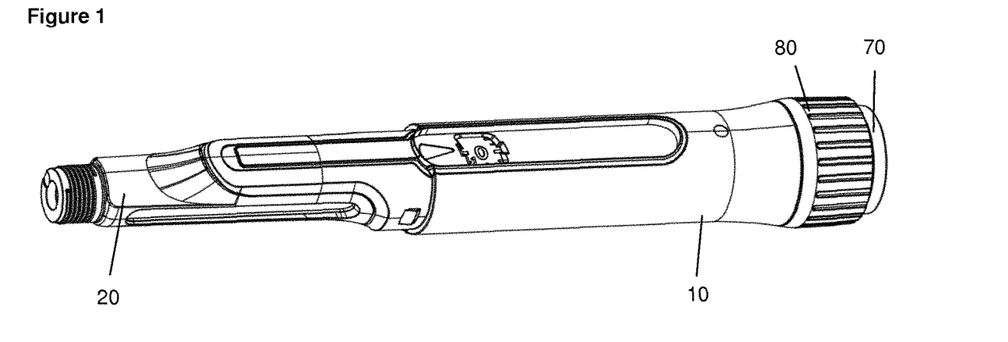
FIG. 1 shows a top view of a drug delivery device.
Figure 2:
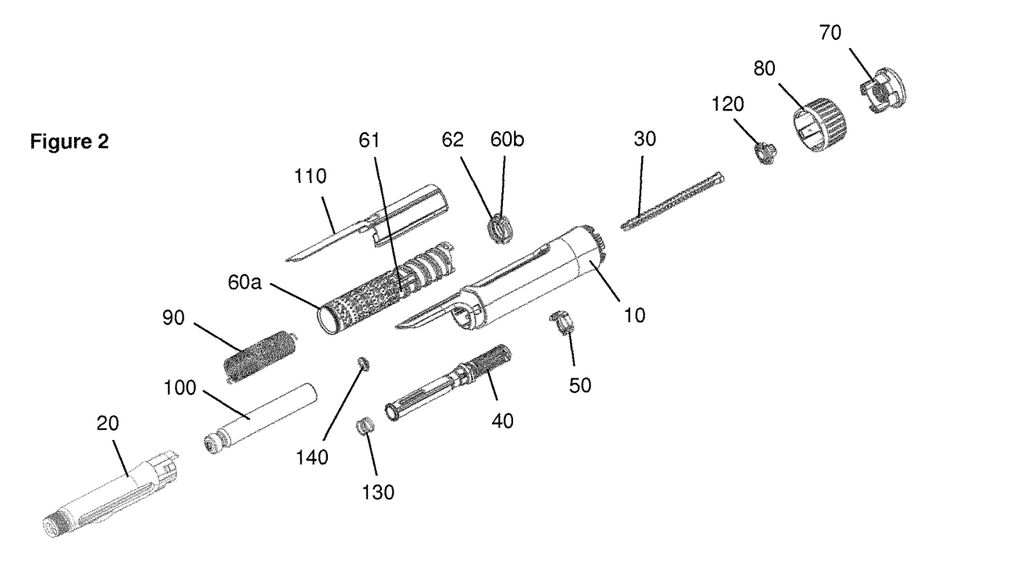
FIG. 2 shows an exploded view of the components of the device of FIG. 1.

FIG. 1 shows a drug delivery device in the form of an injection pen. The device has a distal end (left end in FIG. 1) and a proximal end (right end in FIG. 1). The component parts of the drug delivery device are shown in FIG. 2. The drug delivery device comprises a body or housing 10, a cartridge holder 20, a lead screw (piston rod) 30, a drive sleeve 40, a nut 50, a dose indicator (number sleeve) 60, a button 70, a dial grip or dose selector 80, a torsion spring 90, a cartridge 100, a gauge element 110, a clutch plate 120, a clutch spring 130 and a bearing 140. A needle arrangement (not shown) with a needle hub and a needle cover may be provided as additional components, which can be exchanged as explained above. All components are located concentrically about a common principal axis of the mechanism.

The housing 10 or body is a generally tubular element having a proximal end with an enlarged diameter. The housing 10 provides location for the liquid medication cartridge 100 and cartridge holder 20, windows for viewing the dose number on the number sleeve 60 and the gauge element 110, and a feature on its external surface, e.g. a circumferential groove, to axially retain the dose selector 80. An insert comprises an inner thread engaging the piston rod 30. The housing 10 further has at least one internal, axially orientated slot or the like for axially guiding the gauge element 110. In the embodiment shown in the Figures, the distal end is provided with an axially extending strip partly overlapping cartridge holder 20. The Figures depict the housing 10 as a single housing component. However, the housing 10 could comprise two or more housing components which may be permanently attached to each other during assembly of the device. The drive spring 90 is attached with one end to the housing 10.

The cartridge holder 20 is located at the distal side of housing 10 and permanently attached thereto. The cartridge holder may be a transparent or translucent component which is tubular to receive cartridge 100. The distal end of cartridge holder 20 may be provided with means for attaching a needle arrangement. A removable cap (not shown) may be provided to fit over the cartridge holder 20 and may be retained via clip features on the housing 10.

The piston rod 30 is rotationally constrained to the drive sleeve 40 via a splined interface. When rotated, the piston rod 30 is forced to move axially relative to the drive sleeve 40, through its threaded interface with the insert of housing 10. The lead screw 30 is an elongate member with an outer thread engaging the corresponding thread of the insert of housing 10. The interface comprises at least one longitudinal groove or track and a corresponding protrusion or spline of the driver 40. At its distal end, the lead screw 30 is provided with an interface for clip attachment of the bearing 140.

The drive sleeve 40 is a hollow member surrounding the lead screw 30 and arranged within number sleeve 60. It extends from an interface with the clutch plate 120 to the contact with the clutch spring 130. The drive sleeve 40 is axially movable relative to the housing 10, the piston rod 30 and the number sleeve 60 in the distal direction against the bias of clutch spring 130 and in the opposite proximal direction under the bias of clutch spring 130.

A splined tooth interface with the housing 10 prevents rotation of the drive sleeve 40 during dose setting. This interface comprises a ring of radially extending outer teeth at the distal end of drive sleeve 40 and corresponding radially extending inner teeth of the housing component 10. When the button 70 is pressed, these drive sleeve 40 to housing 10 spline teeth are disengaged allowing the drive sleeve 40 to rotate relative to housing 10. A further splined tooth interface with the number sleeve 60 is not engaged during dialing, but engages when the button 70 is pressed, preventing relative rotation between the drive sleeve 40 and number sleeve 60 during dispense. In a preferred embodiment this interface comprises inwardly directed splines on a flange on the inner surface of the number sleeve 60 and a ring of radially extending outer splines of drive sleeve 40. These corresponding splines are located on the number sleeve 60 and the drive sleeve 40, respectively, such that axial movement of the drive sleeve 40 relative to the (axially fixed) number sleeve 60 engages or disengages the splines to rotationally couple or decouple the drive sleeve 40 and the number sleeve 60.

A further interface of the drive sleeve 40 comprises a ring of ratchet teeth located at the proximal end face of drive sleeve 40 and a ring of corresponding ratchet teeth on the clutch plate 120.

The driver 40 has a threaded section providing a helical track for the nut 50. In addition, a last dose abutment or stop is provided which may be the end of the thread track or preferably a rotational hard stop for interaction with a corresponding last dose stop of nut 50, thus limiting movement of the nut 50 on the driver thread. At least one longitudinal spline of the driver 40 engages a corresponding track of the lead screw 30.

The last dose nut 50 is located between the number sleeve 60 and the drive sleeve 40. It is rotationally constrained to the number sleeve 60, via a splined interface. It moves along a helical path relative to the drive sleeve 40, via a threaded interface, when relative rotation occurs between the number sleeve 60 and drive sleeve 40 which is during dialing only. As an alternative, the nut 50 may be splined to the driver 40 and threaded to the number sleeve 60. A last dose stop is provided on nut 50 engaging a stop of drive sleeve 40 when a dose is set corresponding to the remaining dispensable amount of medicament in the cartridge 100.

The dose indicator or number sleeve 60 is a tubular element. The number sleeve 60 is rotated during dose setting (via dose selector 80) and dose correction and during dose dispensing by torsion spring 90. The number sleeve 60 is axially constrained to the housing 10, e.g. by snap engagement of a bead on an inner housing surface with a groove on an outer number sleeve surface, while being free to rotate relative to the housing 10. The drive spring 90 is attached with one end to the number sleeve 60. Further, the number sleeve 60 is in threaded engagement with the gauge element 110 such that rotation of the number sleeve causes axial displacement of the gauge element 110. Together with gauge element 110 the number sleeve 60 defines a zero position ('at rest') and a maximum dose position. Thus, the number sleeve 60 may be seen as a dose setting member.

The number sleeve 60 comprises a number sleeve lower 60a which is rigidly fixed to a number sleeve upper 60b during assembly, e.g. by snap engagement, to form the number sleeve 60. Number sleeve lower 60a and number sleeve upper 60b are separate components to allow charging of drive spring 90 during assembly at a stage when the number sleeve lower 60a and number sleeve upper 60b are detached. In addition, the separation of the number sleeve into two component parts which are fixed to each other only during assembly simplifies number sleeve mold tooling and assembly of the drug delivery device. The number sleeve lower 60a is marked with a sequence of numbers, which are visible through the gauge element 110 and the openings in the housing 10, to denote the dialed dose of medicament. Further, the number sleeve lower 60a has a portion with an outer thread engaging the gauge element 110. End stops are provided at the opposite ends of thread to limit relative movement with respect to the gauge element 110. In more detail, the distal end of the thread on number sleeve lower 60a defines a minimum position stop 61 and a proximal thread end on number sleeve upper 60b defines a maximum position stop 62. The gauge element 110 has an internal thread form engaging the thread on number sleeve 60, which thread form abuts stops 61 and 62, respectively, when the drug delivery device is in a minimum dose position or in a maximum dose position.

Clutch features which have the form of a ring of splines are provided inwardly directed on number sleeve upper 60*b* for engagement with splines of the button 70 during dose setting and dose correction. A clicker arm is provided on the outer surface of number sleeve 60 which interacts with the drive sleeve 40 and the gauge member 110 for generating a feedback signal. In addition, the number sleeve lower 60*a* is rotationally constrained to the nut 50 and to the clutch plate 120 via a splined interface comprising at least one longitudinal spline. Further, number sleeve lower 60*a* comprises an interface for attachment of the torsion spring 90.

The button 70 which forms the proximal end of the device is permanently splined to the dose selector 80. A central stem extends distally from the proximal actuation face of the button 70. The stem is provided with a flange carrying the splines for engagement with splines of the number sleeve upper 60*b*. Thus, it is also splined via splines to the number sleeve upper 60*b* when the button 70 is not pressed, but this spline interface is disconnected when the button 70 is pressed. The button 70 has a discontinuous annular skirt with splines. When the button 70 is pressed, splines on the button 70 engage with splines on the housing 10, preventing rotation of the button 70 (and hence the dose selector 80) during dispense. These splines disengage when the button 70 is released, allowing a dose to be dialed. Further, a ring of ratchet teeth is provided on the inner side of button flange for interaction with clutch plate 120.

The dose selector 80 is axially constrained to the housing 10. It is rotationally constrained, via the splined interface, to the button 70. This splined interface which includes grooves interacting with spline features formed by the annular skirt of button 70 remains engaged irrespective of the dose button 70 axial positions. The dose selector 80 or dose dial grip is a sleeve-like component with a serrated outer skirt.

The torsion spring 90 is attached at its distal end to the housing 10 and at the other end to the number sleeve 60. The torsion spring 90 is located inside the number sleeve 60 and surrounds a distal portion of the drive sleeve 40. As will be explained in more detail below, the torsion spring 90 is pre-wound upon assembly into the drug delivery device, such that it applies a torque to the number sleeve 60, even when the mechanism is at zero units dialed, that is in the at rest position. The action of rotating the dose selector 80, to set a dose, rotates the number sleeve 60 relative to the housing 10, and charges the torsion spring 90 further. The torsion spring 90 is a drive spring which drives the number sleeve 60 during dose dispensing, thereby unwinding.

During assembly of the device, the gauge element 110, the number sleeve lower 60*a* and the torsion spring 90 are assembled into the housing 10. The torsion spring 90 is then charged by rotating the number sleeve lower 60*a* e.g. clockwise (when viewed from the proximal end of the device) which causes the gauge element 110 to move in the proximal direction. As the number sleeve upper 60*b* is not yet present, the gauge element 110 will continue to move until it loses engagement with the thread on the number sleeve lower 60*a*. The rotation of number sleeve lower 60*a* continues until the torsion spring 90 has been fully charged, with the gauge element 110 remaining disengaged from the thread of number sleeve lower 60*a*. The number sleeve lower 60*a* is then rotated in the anticlockwise direction and the thread re-engages the gauge element 110. The gauge element 110 then moves in the distal direction until the 0U position is reached with the stop 61 abutting the thread form of gauge element 110. The number sleeve upper 60*b* is then permanently and rigidly clipped onto the number sleeve lower 60*a*, thus providing the maximum dose stop with stop face 62.

Figure 3A:
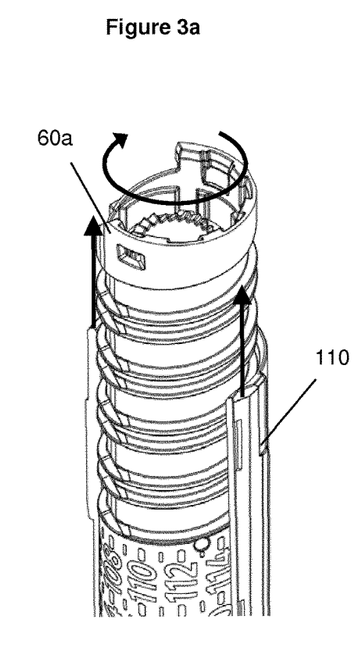
FIG. 3a-d show steps of a method according to an embodiment of the present disclosure.
Figure 3B:
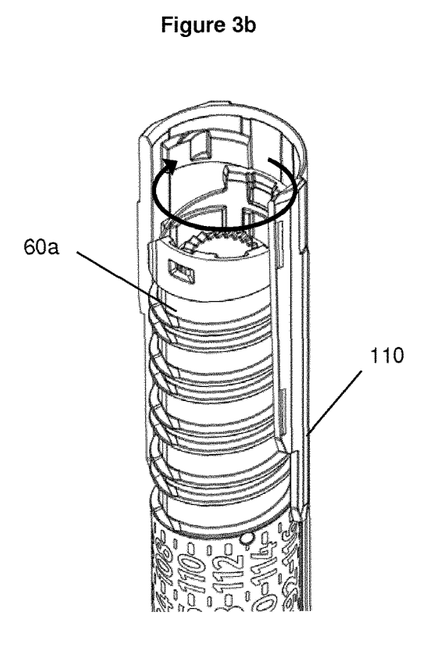
Figure 3C:
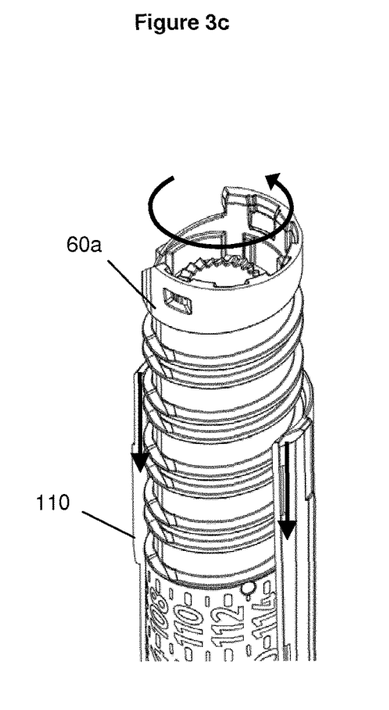
Figure 3D:
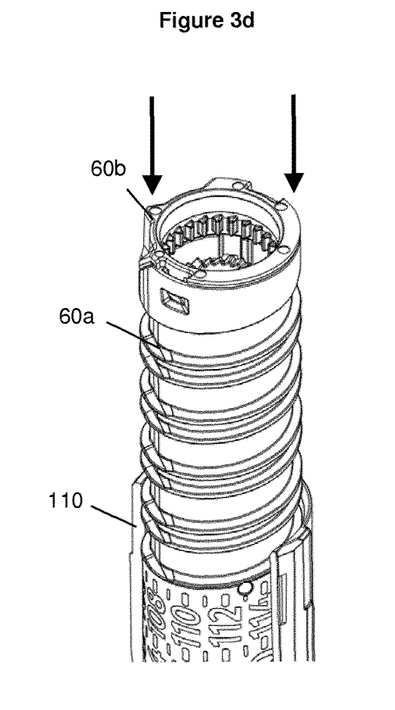

FIGS. 3*a* to 3*d* depict the method of assembling and charging the spring 90. In a first step shown in FIG. 3*a*, the torsion spring 90 is already connected to the number sleeve lower 60*a* and the housing 10. The number sleeve lower 60*a* is rotated during assembly to charge the torsion spring 90 as indicated by an arrow in FIG. 3*a*. The gauge component 110 forms the 0U stop in interaction with the number sleeve lower 60*a* and is required to prevent the torsion spring 90 from unwinding. It is advantageous, to minimize the complexity of the assembly operation, to assemble the gauge component 110 to the number sleeve lower 60*a* prior to charging of torsion spring 90, rather than at some point during charging. The method according to the present disclosure allows the torsion spring 90 to be charged while the gauge element 110 is fitted to the number sleeve lower 60*a*, despite the fact that the number of charging turns is greater than the working range of the gauge element 110 within the thread of number sleeve lower 60*a*. This is achieved by locating the upper ('maximum dose') stop 62 on a separate component, namely the number sleeve upper 60*b*, which is not fitted during charging, allowing the gauge element 110 to disengage from the thread. This is shown in FIG. 3*b*. In FIG. 3*c* the number sleeve lower 60*a* begins to rotate anticlockwise, the gauge element 110 re-engages the thread of number sleeve lower 60*a* and is moved in the distal direction. Then by employing lead-in features, the thread and ultimately the 0U stop is re-engaged when the torsion spring 90 is released. Number sleeve upper 60*b* is then clipped in place as shown in FIG. 3*d*.

If the process is carried out with the device axis vertical and the proximal end uppermost, then gravity may be sufficient to cause the gauge element 110 to re-engage with the thread of number sleeve lower 60*a*. However, a light spring force may be used to push the gauge element 110 into the number sleeve lower 60*a* as it is rotated clockwise and then anticlockwise, ensuring thread re-engagement. Alternatively, the gauge element 110 could be pushed into the number sleeve lower 60*a* only once the clockwise rotation is completed.

The cartridge 100 is received in cartridge holder 20. The cartridge 100 may be a glass ampoule having a moveable rubber bung at its proximal end. The distal end of cartridge 100 is provided with a pierceable rubber seal which is held in place by a crimped annular metal band. In the embodiment depicted in the Figures, the cartridge 100 is a standard 1.5 ml cartridge. The device is designed to be disposable in that the cartridge 100 cannot be replaced by the user or health care professional. However, a reusable variant of the device could be provided by making the cartridge holder 20 removable and allowing backwinding of the lead screw 30 and the resetting of nut 50.

The gauge element 110 of FIGS. 1 and 2 is constrained to prevent rotation but allow translation relative to the housing 10 via a splined interface. The gauge element 110 has a helical feature on its inner surface which engages with the helical thread cut in the number sleeve 60 such that rotation of the number sleeve 60 causes axial translation of the gauge element 110. This helical feature on the gauge element 110 also creates stop abutments against the end of the helical cut in the number sleeve 60 to limit the minimum and maximum dose that can be set.

The gauge element 110 has a generally plate or band like component having a central aperture or window and two flanges extending on either side of the aperture. The flanges are preferably not transparent and thus shield or cover the number sleeve 60, whereas the aperture or window allows viewing a portion of the number sleeve lower 60a. Further, gauge element 110 has a cam and a recess interacting with the clicker arm of the number sleeve 60 at the end of dose dispensing.

The clutch plate 120 is a ring-like component. The clutch plate 120 is splined to the number sleeve 60 via splines. It is also coupled to the drive sleeve 40 via a ratchet interface. The ratchet provides a detented position between the number sleeve 60 and drive sleeve 40 corresponding to each dose unit, and engages different ramped tooth angles during clockwise and anti-clockwise relative rotation. A clicker arm is provided on the clutch plate 120 for interaction with ratchet features of the button 70.

The clutch spring 130 is a compression spring. The axial position of the drive sleeve 40, clutch plate 120 and button 70 is defined by the action of the clutch spring 130, which applies a force on the drive sleeve 40 in the proximal direction. This spring force is reacted via the drive sleeve 40, clutch plate 120, and button 70, and when 'at rest' it is further reacted through the dose selector 80 to the housing 10. The spring force ensures that the ratchet interface between drive sleeve 40 and clutch plate 120 is always engaged. In the 'at rest' position, it also ensures that the button splines are engaged with the number sleeve splines, and the drive sleeve teeth are engaged with teeth of the housing 10.

The bearing 140 is axially constrained to the piston rod 30 and acts on the bung within the liquid medicament cartridge. It is axially clipped to the lead screw 30, but free to rotate.

With the device in the 'at rest' condition as shown in FIG. 1, the number sleeve 60 is positioned against its zero dose abutment with the gauge element 110 and the button 70 is not depressed. Dose marking '0' on the number sleeve 60 is visible through the window of the housing 10 and gauge element 110, respectively.

The torsion spring 90, which has a number of pre-wound turns applied to it during assembly of the device, applies a torque to the number sleeve 60 and is prevented from rotating by the zero dose abutment.

The user selects a variable dose of liquid medicament by rotating the dose selector 80 clockwise, which generates an identical rotation in the number sleeve 60. Rotation of the number sleeve 60 causes charging of the torsion spring 90, increasing the energy stored within it. As the number sleeve 60 rotates, the gauge element 110 translates axially due to its threaded engagement thereby showing the value of the dialled dose. The gauge element 110 has flanges either side of the window area which cover the numbers printed on the number sleeve 60 adjacent to the dialled dose to ensure only the set dose number is made visible to the user.

A specific feature of this disclosure is the inclusion of a visual feedback feature in addition to the discrete dose number display typical on devices of this type. The distal end of the gauge element 110 creates a sliding scale through the window in the housing 10. As an alternative, the sliding scale could be formed using a separate component engaged with the number sleeve 60 on a different helical track.

As a dose is set by the user, the gauge element 110 translates axially, the distance moved proportional to the magnitude of the dose set. This feature gives clear feedback to the user regarding the approximate size of the dose set. The dispense speed of an auto-injector mechanism may be higher than for a manual injector device, so it may not be possible to read the numerical dose display during dispense. The gauge feature provides feedback to the user during dispense regarding dispense progress without the need to read the dose number itself. For example, the gauge display may be formed by an opaque element on the gauge element 110 revealing a contrasting colored component underneath. Alternatively, the revealable element may be printed with coarse dose numbers or other indices to provide more precise resolution. In addition, the gauge display simulates a syringe action during dose set and dispense.

The drive sleeve 40 is prevented from rotating as the dose is set and the number sleeve 60 rotated, due to the engagement of its splined teeth with teeth of the housing 10. Relative rotation must therefore occur between the clutch plate 120 and drive sleeve 40 via the ratchet interface.

The user torque required to rotate the dose selector 80 is a sum of the torque required to wind up the torsion spring 90, and the torque required to overhaul the ratchet interface. The clutch spring 130 is designed to provide an axial force to the ratchet interface and to bias the clutch plate 120 onto the drive sleeve 40. This axial load acts to maintain the ratchet teeth engagement of the clutch plate 120 and drive sleeve 40. The torque required to overhaul the ratchet in the dose set direction is a function of the axial load applied by the clutch spring 130, the clockwise ramp angle of the ratchet teeth, the friction coefficient between the mating surfaces and the mean radius of the ratchet interface.

As the user rotates the dose selector 80 sufficiently to increment the mechanism by one increment, the number sleeve 60 rotates relative to the drive sleeve 40 by one ratchet tooth.

At this point the ratchet teeth re-engage into the next detented position. An audible click is generated by the ratchet re-engagement, and tactile feedback is given by the change in torque input required.

Relative rotation of the number sleeve 60 and the drive sleeve 40 is allowed. This relative rotation also causes the last dose nut 50 to travel along its threaded path, towards its last dose abutment on the drive sleeve 40.

With no user torque applied to the dose selector 80, the number sleeve 60 is now prevented from rotating back under the torque applied by the torsion spring 90, solely by the ratchet interface between the clutch plate 120 and the drive sleeve 40. The torque necessary to overhaul the ratchet in the anti-clockwise direction is a function of the axial load applied by the clutch spring 130, the anti-clockwise ramp angle of the ratchet, the friction coefficient between the mating surfaces and the mean radius of the ratchet features. The torque necessary to overhaul the ratchet must be greater than the torque applied to the number sleeve 60 (and hence clutch plate 120) by the torsion spring 90. The ratchet ramp angle is therefore increased in the anti-clockwise direction to ensure this is the case whilst ensuring the dial-up torque is as low as possible.

The user may now choose to increase the selected dose by continuing to rotate the dose selector 80 in the clockwise direction. The process of overhauling the ratchet interface between the number sleeve 60 and drive sleeve 40 is repeated for each dose increment. Additional energy is stored within the torsion spring 90 for each dose increment and audible and tactile feedback is provided for each increment dialed by the re-engagement of the ratchet teeth. The torque required to rotate the dose selector 80 increases as the torque required to wind up the torsion spring 90 increases. The torque required to overhaul the ratchet in the anti-clockwise direction must therefore be greater than the torque applied to the number sleeve 60 by the torsion spring 90 when the maximum dose has been reached.

If the user continues to increase the selected dose until the maximum dose limit is reached, the number sleeve 60 engages with its maximum dose abutment on the maximum dose abutment of gauge element 110. This prevents further rotation of the number sleeve 60, clutch plate 120 and dose selector 80.

Depending on how many increments have already been delivered by the mechanism, during selection of a dose, the last dose nut 50 may contact its last dose abutment with stop face of the drive sleeve 40. The abutment prevents further relative rotation between the number sleeve 60 and the drive sleeve 40, and therefore limits the dose that can be selected. The position of the last dose nut 50 is determined by the total number of relative rotations between the number sleeve 60 and drive sleeve 40, which have occurred each time the user sets a dose.

With the mechanism in a state in which a dose has been selected, the user is able to deselect any number of increments from this dose. Deselecting a dose is achieved by the user rotating the dose selector 80 anti-clockwise. The torque applied to the dose selector 80 by the user is sufficient, when combined with the torque applied by the torsion spring 90, to overhaul the ratchet interface between the clutch plate 120 and drive sleeve 40 in the anti-clockwise direction. When the ratchet is overhauled, anti-clockwise rotation occurs in the number sleeve 60 (via the clutch plate 120), which returns the number sleeve 60 towards the zero dose position, and unwinds the torsion spring 90. The relative rotation between the number sleeve 60 and drive sleeve 40 causes the last dose nut 50 to return along its helical path, away from the last dose abutment.

With the mechanism in a state in which a dose has been selected, the user is able to activate the mechanism to commence delivery of a dose. Delivery of a dose is initiated by the user depressing the button 70 axially in the distal direction.

When the button 70 is depressed, splines between the button 70 and number sleeve 60 are disengaged, rotationally disconnecting the button 70 and dose selector 80 from the delivery mechanism, i.e. from number sleeve 60, gauge element 110 and torsion spring 90. Splines on the button 70 engage with splines on the housing 10, preventing rotation of the button 70 (and hence the dose selector 80) during dispense. As the button 70 is stationary during dispense, it can be used in the dispense clicker mechanism. A stop feature in the housing 10 limits axial travel of the button 70 and reacts any axial abuse loads applied by the user, reducing the risk of damaging internal components.

The clutch plate 120 and drive sleeve 40 travel axially with the button 70. This engages the splined tooth interface between the drive sleeve 40 and number sleeve 60, preventing relative rotation between the drive sleeve 40 and number sleeve 60 during dispense. The splined tooth interface between the drive sleeve 40 and the housing 10 disengages, so the drive sleeve 40 can now rotate and is driven by the torsion spring 90 via the number sleeve 60, and clutch plate 120.

Rotation of the drive sleeve 40 causes the piston rod 30 to rotate due to their splined engagement, and the piston rod 30 then advances due to its threaded engagement to the housing 10. The number sleeve 60 rotation also causes the gauge element 110 to traverse axially back to its zero position whereby the zero dose abutment stops the mechanism.

Tactile feedback during dose dispense is provided via the compliant cantilever clicker arm integrated into the clutch plate 120. This arm interfaces radially with ratchet features on the inner surface of the button 70, whereby the ratchet tooth spacing corresponds to the number sleeve 60 rotation required for a single increment dispense. During dispense, as the number sleeve 60 rotates and the button 70 is rotationally coupled to the housing 10, the ratchet features engage with the clicker arm to produce an audible click with each dose increment delivered.

Delivery of a dose continues via the mechanical interactions described above while the user continues to depress the button 70. If the user releases the button 70, the clutch spring 130 returns the drive sleeve 40 to its 'at rest' position (together with the clutch plate 120 and button 70), engaging the splines between the drive sleeve 40 and housing 10, preventing further rotation and stopping dose delivery.

During delivery of a dose, the drive sleeve 40 and number sleeve 60 rotate together, so that no relative motion in the last dose nut 50 occurs. The last dose nut 50 therefore travels axially relative to the drive sleeve 40 during dialing only.

Once the delivery of a dose is stopped, by the number sleeve 60 returning to the zero dose abutment, the user may release the button 70, which will re-engage the spline teeth between the drive sleeve 40 and housing 10. The mechanism is now returned to the 'at rest' condition.

At the end of dose dispensing, additional audible feedback is provided in the form of a 'click', distinct from the 'clicks' provided during dispense, to inform the user that the device has returned to its zero position via the interaction of the clicker arm on the number sleeve 60 with the ramp on the drive sleeve 40 and the cam and the recess on the gauge element 110. This embodiment allows feedback to only be created at the end of dose delivery and not created if the device is dialed back to, or away from, the zero position.

REFERENCE NUMERALS

| | |
|---|---|
| 10 | housing (casing) |
| 20 | cartridge holder |
| 30 | piston rod (lead screw) |
| 40 | drive sleeve |
| 50 | nut |
| 60 | dose setting element |
| 60a | number sleeve lower |
| 60b | number sleeve upper |
| 61 | minimum stop |
| 62 | maximum stop |
| 70 | button |
| 80 | dose selector |
| 90 | torsion spring |
| 100 | cartridge |
| 110 | gauge element |
| 120 | clutch plate |
| 130 | clutch spring |
| 140 | bearing |

The invention claimed is:

1. A method for assembling a drive spring in a drug delivery device, the method comprising the steps:
 a) attaching a torsion spring with a first end to a first rotationally fixed component part and with a second end to a rotatable component part, the rotatable component part being:
  in threaded engagement with a second rotationally fixed component part with a first rotational stop,
  rotatable in a first direction toward the first rotational stop and in a second direction away from the first rotational stop, the first rotational stop configured to prevent rotation of the rotatable component part relative to the second rotationally fixed component part in the first direction beyond the first rotational stop, wherein the torsion spring is charged by rotation of the rotatable component part in the second direction and the torsion spring is released by rotation of the rotatable component part in the first direction, b) rotating the rotatable component part away from the first rotational stop in the second direction until the rotatable component part disengages from the second rotationally fixed component part, c) further rotating the rotatable component part in the second direction with the rotatable component part disengaged from the second rotationally fixed component part, d) rotating the rotatable component part in the first direction such that the rotatable component part re-engages the second rotationally fixed component part, and e) attaching a second rotational stop to the rotatable component part or the second rotationally fixed component part to prevent rotation of the rotatable component part relative to the second rotationally fixed component part in the second direction beyond the second rotational stop.

2. The method according to claim 1, wherein in step a) the rotatable component part is positioned relative to the second rotationally fixed component part such that the first rotational stop is in effect.

3. The method according to claim 1, wherein the first rotationally fixed component part is rotationally coupled to the second rotationally fixed component part to prevent relative rotation.

4. The method according to claim 3, wherein at least during steps b) and c) the rotatable component part is engaged by a rotatable tool while the first rotationally fixed component part is rotationally constrained by a further tool.

5. The method according to claim 1, wherein the rotatable component part is rotated in step d) by the torsion spring and/or by a rotatable tool.

6. The method according to claim 1, wherein the rotatable component part is rotated in step d) until the first rotational stop prevents rotation of the rotatable component part relative to the second rotationally fixed component part in the first direction.

7. The method according to claim 1, wherein in step e) the second rotational stop is permanently attached to the rotatable component part.

8. The method according to claim 1, wherein in step a) the torsion spring is axially compressed between the first rotationally fixed component part and the rotatable component part.

9. The method according to claim 1, further comprising the steps of assembling a cartridge holder, piston rod, a drive sleeve, a nut, a button, a dose selector, a clutch plate and/or a clutch spring.

* * * * *